(12) United States Patent
Alroy et al.

(10) Patent No.: US 7,266,405 B1
(45) Date of Patent: Sep. 4, 2007

(54) COMPACT ELECTRODE ASSEMBLY FOR A PORTABLE ECG SIGNALING DEVICE

(75) Inventors: Yoram Alroy, Tel Aviv (IL); Herbert Reinhold, Arnold, MD (US)

(73) Assignee: SHL Telemedicine International Ltd., Tel Aviv (IL)

( * ) Notice: Subject to any disclaimer, the term of this patent is extended or adjusted under 35 U.S.C. 154(b) by 466 days.

(21) Appl. No.: 10/069,361

(22) PCT Filed: Aug. 23, 2000

(86) PCT No.: PCT/IL00/00506

§ 371 (c)(1),
(2), (4) Date: Jun. 5, 2002

(87) PCT Pub. No.: WO01/13791

PCT Pub. Date: Mar. 1, 2001

(30) Foreign Application Priority Data

Aug. 23, 1999 (IL) .................................. 131538

(51) Int. Cl.
*A61B 5/0408* (2006.01)
(52) U.S. Cl. ........................ 600/386; 607/152
(58) Field of Classification Search .......... 600/372, 600/382, 388–390, 393
See application file for complete search history.

(56) References Cited

U.S. PATENT DOCUMENTS

| | | | |
|---|---|---|---|
| 4,004,578 A | 1/1977 | Palmius | |
| 4,082,087 A | 4/1978 | Howson | |
| 4,522,211 A | 6/1985 | Bare et al. | |
| 4,763,660 A | 8/1988 | Kroll et al. | |
| 5,029,590 A | 7/1991 | Allain et al. | |
| 5,058,597 A | 10/1991 | Onoda et al. | |
| 5,184,620 A * | 2/1993 | Cudahy et al. | 600/382 |
| 5,305,746 A | 4/1994 | Fendrock | |
| 5,339,823 A | 8/1994 | Reinhold, Jr. | |
| 5,341,806 A * | 8/1994 | Gadsby et al. | 600/393 |
| 5,465,727 A | 11/1995 | Reinhold, Jr. | |
| 5,466,244 A | 11/1995 | Morgan | |
| 5,505,202 A * | 4/1996 | Mogi et al. | 600/390 |
| 5,514,862 A | 5/1996 | Salzano | |
| 5,724,984 A | 3/1998 | Arnold et al. | |
| 6,115,623 A * | 9/2000 | McFee | 600/372 |
| 6,486,779 B1 | 11/2002 | Alroy | |

FOREIGN PATENT DOCUMENTS

| | | |
|---|---|---|
| DE | 36 37 956 A1 | 6/1987 |
| GB | 2 287 882 A | 10/1995 |
| WO | WO94/26350 A1 | 11/1994 |
| WO | WO99/45516 A1 | 9/1999 |
| WO | WO 99/45516 A1 | 9/1999 |

* cited by examiner

*Primary Examiner*—Carl Layno
*Assistant Examiner*—Kristen Droesch Mullen
(74) *Attorney, Agent, or Firm*—Browdy and Neimark, PLLC

(57) ABSTRACT

An electrode assembly (10) for a portable ECG signaling device, comprises a thin, flexible electrode support (11) supporting thereon a plurality of electrodes in spaced relationship. The electrodes ($V_1$, $V_2$, $V_3$, $V_4$, $V_5$ and $V_6$, LA, RA, LL) are configured for producing a twelve-lead electrocardiogram, and the electrode assembly is foldable into a compact assembly when not in use.

22 Claims, 5 Drawing Sheets

COMPACT ELECTRODE ASSEMBLY FOR A PORTABLE ECG SIGNALING DEVICE

FIELD OF THE INVENTION

This invention relates to a portable ECG signaling device.

BACKGROUND OF THE INVENTION

Patients having a history of medical ailments not infrequently subscribe to a medical monitoring service on an ambulatory basis. Upon effecting communication with a monitoring unit, the patient is frequently required to undertake an interactive dialog with medical personnel at the monitoring unit so as to enable the medical personnel to diagnose the patient's medical symptoms. Since many of those who are particularly at risk suffer from heart-disease, an ECG is usually one of the first tests which should be carried out. To this end, much effort has been directed to the provision of portable instruments for allowing a patient to carry out an ECG on himself. At their most rudimentary, such instruments comprises a pair of electrodes, which are held against a patient's body, usually near his chest to detect an electrical voltage indicative of the electrical activity of the heart. The resulting current waveform response permits partial determination of the patient's cardiac health. A more detailed determination may be realized by using more than two electrodes and portable devices are known having, for example, ten electrodes mounted on a common carrier and amenable to placement on a patient's chest area by the patient with minimum effort.

U.S. Pat. No. 5,339,823 (Reinhold, Jr.) discloses a method and device for obtaining electrical heart activity of an individual in a form capable of producing a twelve-lead electrocardiogram of an individual. The device includes a portable electrode support having an array of six non-adhesive precordial electrodes fixed thereon at predetermined positions within the array which correspond with the Wilson precordial leads for the individual. The device also includes a right arm electrode, a left arm electrode, a left leg electrode and circuitry for converting the electrical heart activity of the individual obtained by said electrodes into a form capable of producing a twelve-lead electrocardiogram. The method includes the steps of applying the left leg, left arm and right arm electrode to the skin of the individual at locations such that the circuitry can be electrically operable to obtain leads I, II, III, AVR, AVL, and AVF therefrom. Huma pressure is applied to engage the array of six precordial electrodes with the skin of the chest of the individual in an operative relation, and circuitry is operated for a time sufficient to obtain electrical heart activity of the individual in a form capable of producing an electrocardiogram.

It will be appreciated that no less important than the technical suitability of such ECG transmitters, is that they must be instantly accessible in a moment of crisis. In the first instance, the required accessibility can only be realized by a portable device. However, experience indicates that this in itself is often not enough. Most people find it difficult to function and to preserve their mental health if they live in constant fear of their mortality. Particularly, those who have a history of heart disease or other serious illness can do without constant reminders that they might need to perform an instant ECG in the street or elsewhere remote from hospital or home. As a result, there are many who consign the thought to their subconscious and it is then but a small step to relegating it to their unconscious altogether.

Such a likelihood would be reduced if the ECG transmitter were not only portable but were so disguised as to be indistinguishable from an everyday item which, in any case, the patient would carry on his or her person. Our co-pending International publication no. WO 99/45516 discloses fixedly embedding the ECG electrodes within a wallet containing a microphone, transceiver and processing circuit. However, such an arrangement is limited in size by virtue of the compactness of the wallet, which must be preserved. This requires, in practice, that only two ECG leads are provided, these being sewn into the inside fabric of the wallet and militates against the provision of a full ECG monitoring capability requiring an array of displaced electrodes spanning a patient's chest area.

U.S. Pat. No. 5,724,984 discloses a multi-segment ECG electrode including a flexible basepad, a central segment defined on a surface of the basepad, and exterior segments defined on the surface of the basepad. The exterior segments may be sized, shaped and positioned relative to the central segment so that an average position of the exterior segments approximates a position of the central segment.

U.S. Pat. No. 4,763,660 discloses a flexible and disposable electrode belt device for receiving and transmitting electric current or voltage for use on the body of a patient. The belt has a unitary layered body structure that is releasably secured to the patient. The belt device body structure has a terminal end that is connectable for communication with medical therapeutic and diagnostic apparatus. The layered body structure further includes a plurality of flexible non-conductive and conductive layers, a conductive network having electrode contact areas at predetermined positions and conductive adhesive members to removably hold the device to a patient and to, thereby, transfer electrical signals between predetermined patient body locations and the medical therapeutic and diagnostic apparatus.

U.S. Pat. No. 4,082,087 discloses a body contact electrode structure for deriving electrical signals due to physiological activity, comprising a thin, flexible body of non-conductive material having one or more wells therein. A flexible conductive member which provides an electrode is disposed at the bottom of each well. The spacing between a plurality of electrodes, which can provide bipolar and ground inputs to the medical electronic instrument, is precisely determined by virtue of the disposition of the electrodes in the wells. The electrode structure provides contact with a body surface, usually the skin. To facilitate the contact a conductive jelly is used. This conductive jelly is received in the wells. It makes contact with the electrodes. Ribs are provided in the regions between the electrodes, which form a seal at the skin so as to prevent the flow of conductive fluid between electrodes; thus preventing short circuits. The flexibility of the structure provides for comfort and reliable long term attachment and also for maintaining the contact of the electrodes and sealing ribs with the skin as the skin and muscle beneath, flex.

U.S. Pat. No. 4,004,578 discloses an expendable electrocardiograph electrode comprising a thin metallic carrier member coated on the surface to be applied to the skin with an adhesive and having a plurality of metallic contact spikes projecting from the coated surface which spikes are devised to penetrate into the skin. The coated and spiked surface is covered by at least one pull-off foil protecting same together with the spikes against environmental influences. On the carrier member, a transverse upwardly directed flange is, provided for attachment to an electrocardiographic apparatus.

U.S. Pat. No. 5,305,746 discloses a disposable, pre-gelled, self-prepping electrode having an array or mat of flexile tines which serve to part the high impedance outer layers of skin to expose the low impedance, blood enriched layers without scratching or abrading. The tines are preferably imbedded in a conductive gel layer. In an alternative embodiment, a self prepping layer of flexile tines embedded in gel may be a single disposable self-prepping layer that is mounted over a permanent electrode.

GB 2 287 882 discloses a flexible sheet having ECG connecting leads enclosed within the sheet to a point close to their desired anatomical destination and that can be rolled up for storage. Essentially, this reference teaches a device that eliminates the tangling of wires which is perceived to be a problem with standard ECG leads, although no specific mention is made that the device disclosed therein is suitable for a 12 lead electrode assembly. In any event, whilst suggestion is made in GB 2 287 882 to direct the ECG leads to a point close to their desired anatomical destination, all that is meant thereby is that the wires constituting the ECG leads protrude from appropriate edges of the electrode support so as to most easily directed to appropriate parts of the body. GB 2 287 882 does not teach a flexible electrode support for supporting on the electrode support itself clinically pre-positioned electrodes in proper spaced relationship for placing directly against a patient's chest so as to produce an electrocardiogram.

It thus emerges that the prior art relates to disposable electrodes that are flexible but that the issues of compactness and especially the ability to fold the electrode are not addressed in the prior art.

SUMMARY OF THE INVENTION

It is an object of the invention to provide a portable compact electrode assembly for a portable ECG monitor allowing standard twelve-lead ECG measurements to be carried out.

This objective is realized in accordance with a broad aspect of the invention by means of an electrode assembly for a portable ECG signaling device, comprising:

a thin, flexible electrode support supporting a plurality of electrodes at least some of which are constructed on the electrode support in proper spaced relationship for producing electrical contact with respective areas of a patient's chest for producing an electrocardiogram when the electrode assembly is placed directly against the patient's chest;

characterized in that:

the flexible support comprises a plurality of foldable sections, whereby the electrode assembly can be folded into a compact unit prior to or after use.

According to a preferred embodiment, the electrode assembly is coupled to an ECG transmitter embedded with a wallet and having controls accessible from inside the wallet. Such a wallet is provided with pockets for accommodating the cash, credit cards and so on in known manner so that the patient who carries it is psychologically immune from the uncomfortable thought that anything medical is associated therewith.

In order to allow the patient to relay the ECG signal to a remote monitoring unit, a vocalizing unit may be provided for converting the ECG signal to a representative acoustic signal that can be sent over the telephone to the monitoring unit. Alternatively, the ECG signal may be modulated on to an r.f. carrier signal for direct transmission with the monitoring unit, thus not requiring that the patient be in ready access with a telephone.

BRIEF DESCRIPTION OF THE DRAWINGS

Preferred embodiments of the invention will now be described, by way of non-limiting example only, with reference to the accompanying drawings, in which.

DETAILED DESCRIPTION OF THE INVENTION

Figure 1:
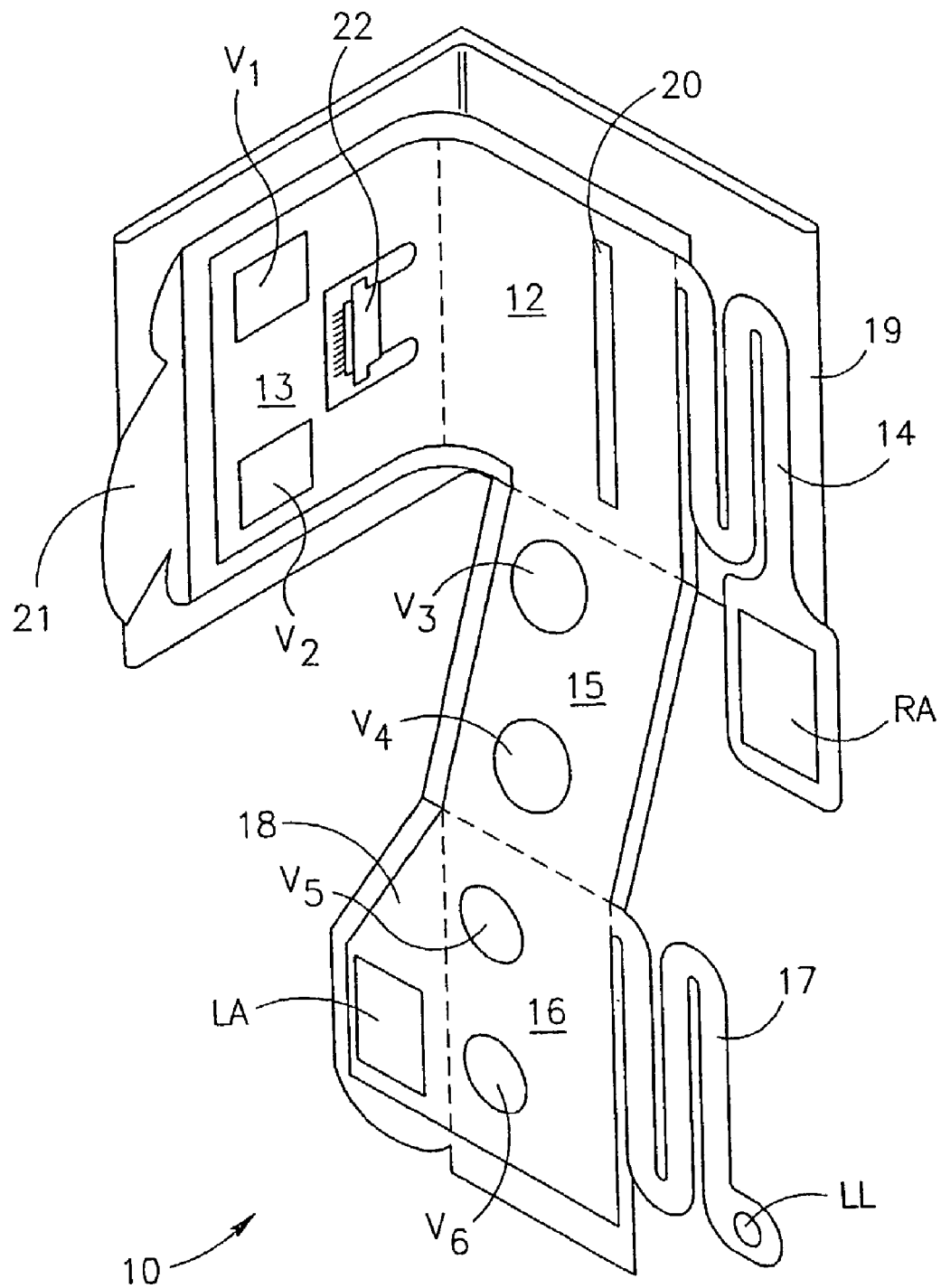
FIG. 1 shows pictorially an ECG electrode assembly according to the invention embedded within a wallet.

FIG. 1 shows pictorially a portable compact electrode assembly depicted generally as 10 comprising a thin, flexible electrode support 11 adapted to produce a 12-lead electrocardiogram in a manner similar to that shown in U.S. Pat. No. 5,339,823. The flexible support 11 comprises a first, rectangular section 12 abutting a second, rectangular section 13 on one side thereof and, on an opposite side thereof, a serpentine strip 14 supporting an electrode RA. A lower edge of the first rectangular section 12 abuts a third rectangular section 15, which in turn abuts at a lower edge thereof a fourth rectangular section 16. The fourth rectangular section 16 abuts at a first side edge thereof a serpentine strip 17 supporting an electrode LL and abuts at a second, opposing side edge thereof a substantially trapezoidal section 18. Contiguous sections may be folded along their common edges, shown dotted in the figure. By such means, the electrode support can be folded into a compact unit that can easily be accommodated inside a wallet 19. Specifically, the serpentine strip 17 and the trapezoidal section 18 are folded inwards along their respective fold lines so as to lie flat on the fourth rectangular section 16. Likewise, the serpentine section 14 is folded along its fold line so as to lie flat on the first rectangular section 12. The fourth rectangular section 16 is then folded inwardly along its fold line so as to lie flat on the third rectangular section 15 which is likewise folded inwardly so as to lie flat on the first rectangular section 12. This having been done, the second rectangular section 13 is folded inwardly on to the now packed second, third and fourth rectangular sections including the adjoining serpentine strips 14 and 17 and the trapezoidal section 18. The first rectangular section 12 is provided with a slot 20, which is so located as to remain exposed even when the serpentine section 14 is folded and accommodates a flap 21 adjoining a side edge of the second rectangular section 13. By such means, the electrode unit 10 may be folded into a compact unit and the flap 21 tucked into the slot 20 so as to prevent the folded electrode unit from opening. The electrode unit 10 may then be carried separately in a person's pocket, for example, or, as noted above, may be accommodated within a wallet so as to provide further protection and ready accessibility. A ribbon connector 22 is attached to the electrodes for removably connecting to the electrode assembly 10 an electronic circuit described below with reference to FIGS. 3 and 4 of the drawings.

ECG leads on the various sections of the electrode unit 11 are referenced by their universally adopted symbols $V_1$, $V_2$, $V_3$, $V_4$, $V_5$ and $V_6$, LA, RA and LL. The electrodes are screen-printed on to the electrode support 11, although any other suitable method for fixing the electrodes to a flexible, insulating liner may be used.

Figure 2:
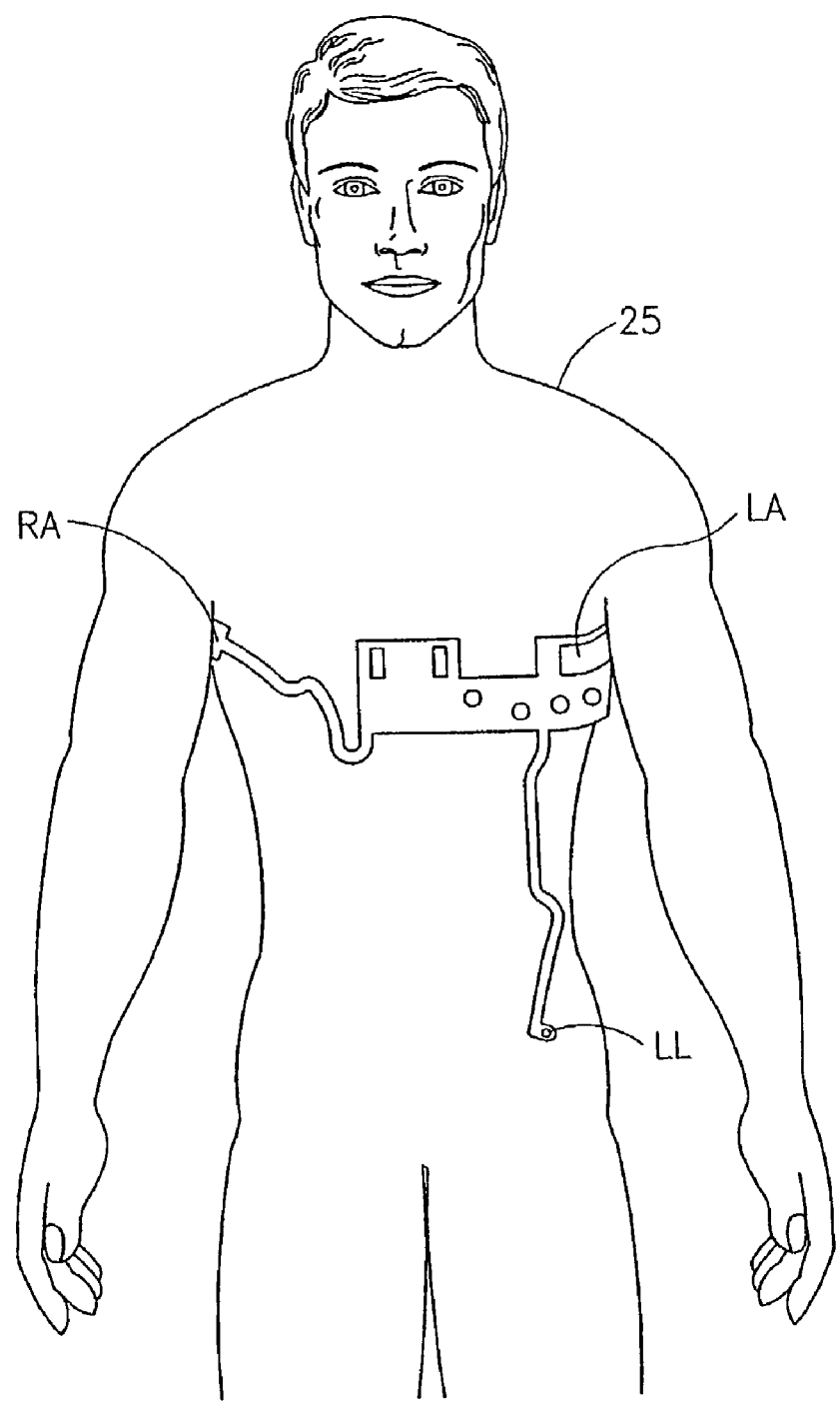
FIG. 2 shows pictorially the ECG assembly when in use.

FIG. 2 shows how the electrode assembly 10 is used for the determination of a full twelve-electrode ECG measurement. A patient 25 unfolds the electrode support 11 and affixes the second rectangular section 13 against his or her chest so that the leads $V_1$ and $V_2$ are substantially symmetrically disposed about his or her vertebrae. To this end, there are provided on each of the leads an electrically conductive, adhesive gel (not shown) which may, if desired, be covered with a wax liner that may be peeled off before use. The gel is specifically formulated to adhere to the patient's skin and to provide good electrical connection whilst allowing painless removal after use. Having affixed the two leads $V_1$ and $V_2$, the four leads $V_3$, $V_4$, $V_5$ and $V_6$ are now disposed on the patient's left rib cage, being mutually displaced by the required distance appropriate to the patient so that the six leads $V_1$ to $V_6$ serve as Wilson precordial electrodes. The dimensions of the electrode support 11 are such that for a given patient, the electrode LA fits under the patient's left armpit, whilst the serpentine electrode RA is fully extended so as to be held under the patient's right armpit. The serpentine lead LL is then stretched and fitted near the patient's waist, typically being held in place using adhesive gel or by a belt (not shown).

Figure 3:
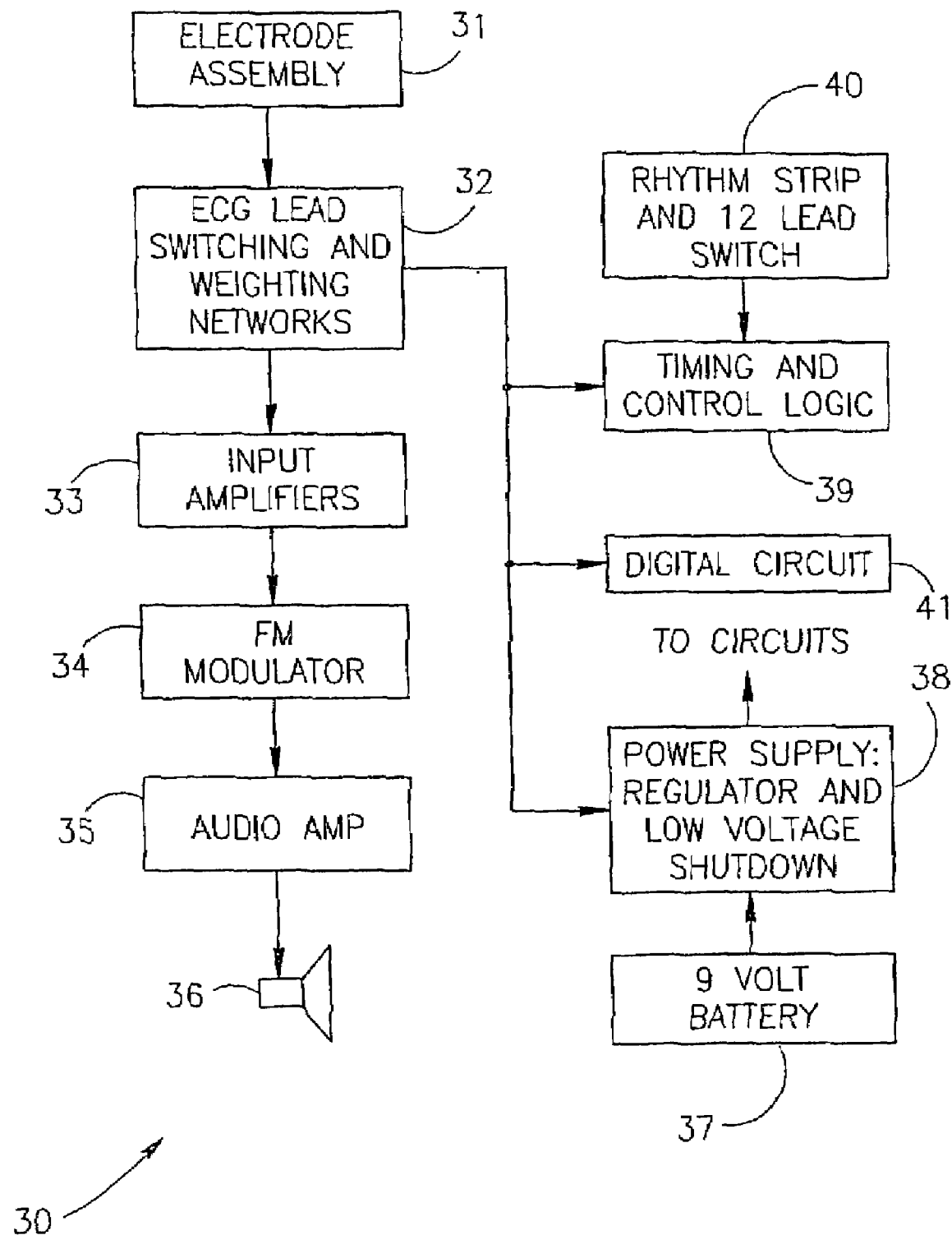
FIGS. 3 and 4 are block diagrams of alternative embodiments showing functionally the principal components in an ECG signaling device utilizing the ECG electrode assembly shown in FIGS. 1 and 2.

FIG. 3 shows functionally an ECG signaling device 30 according to a first embodiment, comprising an electrode assembly 31 including an electrode array, waist and right-arm electrodes. The electrode array is dimensioned for placement against a patient's bare chest and, to this end, electrode assemblies are provided being suitably dimensioned for patients of various sizes. Furthermore, owing to anatomical differences between men and women, different electrode assemblies are preferably supplied to men and women. The electrode assembly 31 is coupled to an ECG lead switching and weighting network 32 which permits the proper selection of electrodes as well as lead weighting to produce a sequential selection of I, II, III, AVR, AVL, AVF, $V_1$, $V_2$, $V_3$, $V_4$, $V_5$ and $V_6$ ECG leads. The output of the ECG lead switching and weighting network 32 is coupled to an amplifier 33, which in turn is coupled to a frequency modulator 34 for converting the analog ECG signal to a representative frequency signal typically centered around 1700 Hz and frequency modulated by the patient's ECG signal. The variable frequency voltage is fed to an audio amplifier 35 whose output is fed to a loudspeaker 36, which together constitute a vocalizing unit for converting the ECG signal to an equivalent acoustic signal, which may be fed over the telephone line to a remote monitoring unit (not shown). Alternatively, the ECG signal may be digitized and transmitted digitally.

The ECG signaling device 30 is powered by means of an internal 9 volt battery 37 connected to a power supply 38 via a normally open switch (not shown). Closing the switch thus connects a regulated battery voltage to the various components of the ECG signaling device 30 so that a modulated tone representative of an ECG rhythm strip is output by the loudspeaker 36 for so long as the pushbutton switch 39 is depressed. The battery 37 may be removably mounted in a casing of the ECG signaling device 30 so as to be replaceable, or they may be irremovable in which case the ECG signaling device 30 must be discarded when the battery 37 is spent. The power supply includes a voltage regulator for proving a regulated voltage for the analog and digital components within the ECG signaling device 30. In addition, there is provided a low battery sensor that is adapted to shut down the circuits should the battery voltage decrease to the point where the regulated voltage or the performance of the device might be adversely affected.

A timing and control logic module 39 is coupled to the power supply 38 and to the ECG lead switching and weighting network 32 and include hard-wired logic gates that provide for selection of the proper electrodes and the timing functions of the ECG signaling device 30. Coupled to the timing and control logic module 39 is an enclosure-mounted pushbutton switch 40, which permits the patient to transmit a rhythm strip and 12-lead ECG. All transmissions are internally timed and the pushbuttons are electronically "latched" after depression, to ensure a complete transmission even if the patient's finger slips off the button during transmission. The timing and control logic module 39 could be replaced by a suitably programmed microprocessor, such as contemplated by a digital circuit 41 connected to the ECG lead switching and weighting networks 32. The digital circuit 41 also allows for transmitting the acoustic data as an equivalent digital signal.

Figure 4:
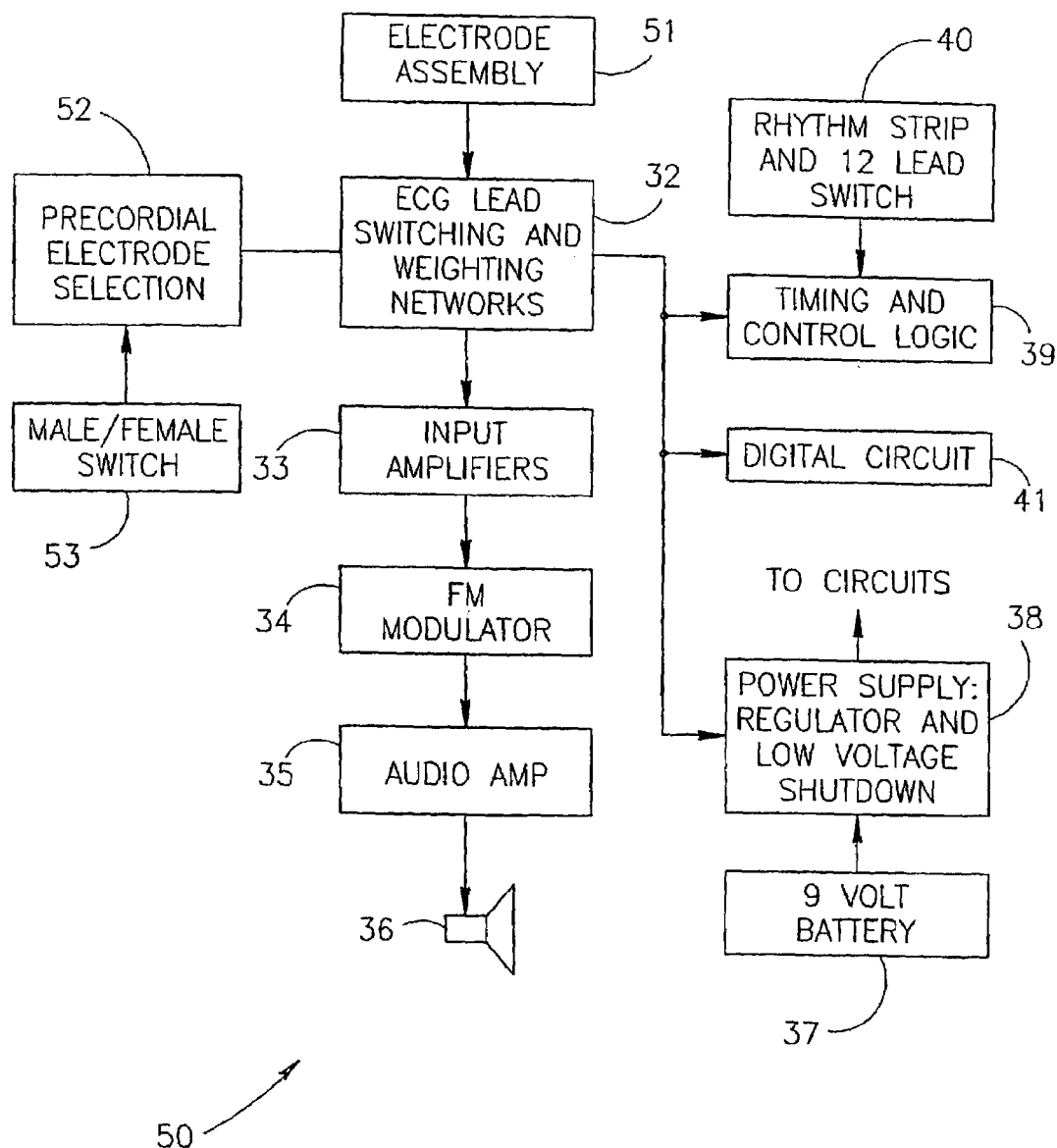

FIG. 4 shows functionally an ECG signaling device 50 according to a second embodiment. Those components that are common to the first embodiment are reference by identical reference numerals. The ECG signaling device 50 comprises an electrode assembly 51 including an electrode array, waist and right-arm electrodes. In this case, a uniform electrode assembly is provided having different electrode arrays, each being properly dimensioned for placement against the bare chest of a respective sized patient. Likewise, different electrode arrays are provided for men and women to account for anatomical differences between the sexes. The electrode assembly 51 is coupled to an ECG lead switching and weighting network 32 which permits the proper selection of electrodes as well as lead weighting to produce a sequential selection of I, II, III, AVR, AVL, AVF, $V_1$, $V_2$, $V_3$, $V_4$, $V_5$ and $V_6$ ECG leads. The output of the ECG lead switching and weighting network 32 is coupled to an amplifier 33, which in turn is coupled to a frequency modulator 34 for converting the analog ECG signal to a representative frequency signal typically centered around 1700 Hz and frequency modulated by the patient's ECG signal. The variable frequency voltage is fed to an audio amplifier 35 whose output is fed to a loudspeaker 36, which together constitute a vocalizing unit for converting the ECG signal to an equivalent acoustic signal, which may be fed over the telephone line to a remote monitoring unit (not shown). Alternatively, digital communication techniques can be employed using a digital circuit 41 connected to the ECG lead switching and weighting networks 32.

In order to ensure selection of the correct electrode array, a precordial electrode selector 52 is coupled to the ECG lead switching and weighting network 32 and is responsive to a male/female selector switch 53. The precordial electrode selector 52 allows for proper selection of the appropriate precordial electrodes $V_1$, $V_2$, $V_3$, $V_4$, $V_5$ and $V_6$ depending on the specified sex of the patient as set by the selector switch 53. To accommodate different chest sizes, two electrode selection areas are provided in the battery compartment. Three jumper blocks are used to select the $V_5$ and $V_6$ electrodes for male and female patients. The male/female selector switch 53 permits the selection of either the male or female $V_1$ and $V_2$ electrodes sets as well as the corresponding pre-selection of $V_4$, $V_5$ and $V_6$. The same $V_3$ electrode is used for male and female patients, regardless of chest size.

The remaining components of the ECG signaling device 50 are identical to those of the ECG signaling device 30 described above with reference to FIG. 3. It is to be noted that the electrode assembly 51 of the second embodiment is designed to be used repeatedly whilst the electrode assembly 31 of the first embodiment may be disposable. Furthermore, providing different electrode arrays for different sized male and female patients obviates the need to print redundant electrodes on the electrode support 11 and reduces the surface area thereof.

The circuitry shown in FIGS. 3 and 4 may be connected to the electrode assembly using a flat, ribbon cable connector connected to the ribbon connector 22 (shown in FIG. 1) or alternatively can be surface mounted using flexible circuit technology on the electrode support 11. This allows for the electrode assembly to be disconnected from the electronic circuit after use and discarded. Another possibility is to surface mount the components on two or more rigid PCBs which are then interconnected by a flexible circuit. This renders the ECG signaling device more compact and amenable to its being embedded within a wallet of normal size.

Figure 5:
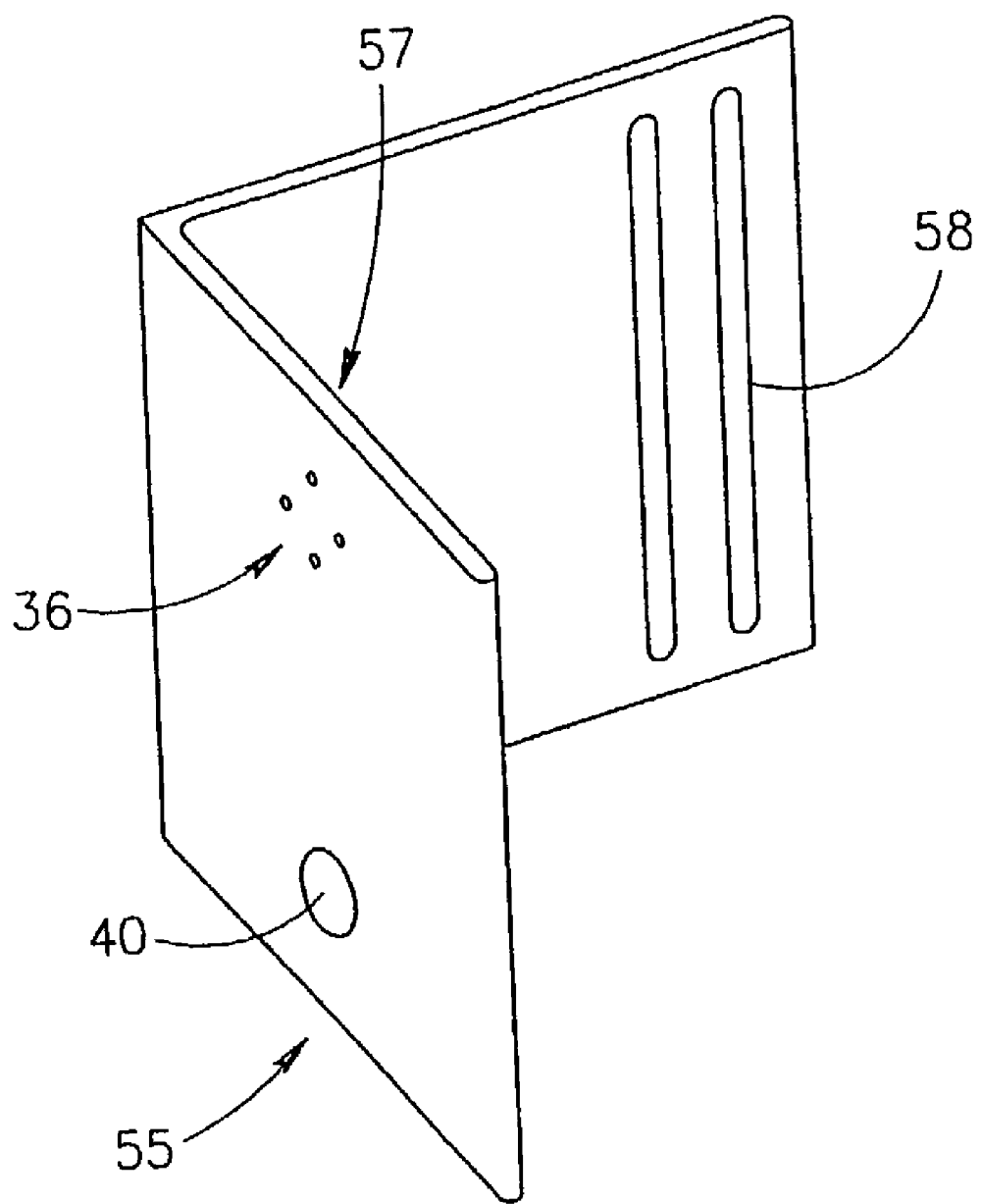
FIG. 5 is a pictorial representation of a wallet having integrally embedded therein an ECG signaling device according to the invention.

Referring to FIG. 5, there is shown a wallet 55 having integrally embedded therein the ECG signaling device 30, the loudspeaker 36 and the pushbutton switch 40 being sewn or otherwise fixed to an outer surface 56 thereof. An inside surface 57 of the wallet is provided in known manner with a plurality of pockets 58 for accommodating notes, credit cards and so on. The remaining circuitry is mounted on a flexible circuit board (not shown), which is secured between the outer and inner surfaces 56 and 57 of the wallet 55. The use of a flexible circuit board allows for the wallet 55 to be folded and subject to moderate deformation as may be applied when the wallet 55 is placed, for example, in a patient's rear trouser pocket and is thereby subject to deformation whenever the patient sits down. In use, the patient must place the electrode array in position and telephone a remote monitoring unit. Connection having been established, the patient now activates the device by depressing the pushbutton switch 40. As noted above, this produces an acoustic signal representative of the ECG rhythm strip and the acoustic signal is transmitted over the telephone line in the usual way.

It will be appreciated that modifications and variations may be effected to the preferred embodiments without departing from the invention.

For example, it is clear that the carrier frequency used to convey acoustic data does not have to be 1700 Hz. As noted, digital communication techniques can be employed instead of transmitting the acoustic data as an analog signal.

Likewise, other common household articles may be adapted to incorporate therein the ECG signaling device or, indeed, other electronic devices so as to serve a dual purpose, thereby increasing the likelihood that their owner will wish to make use thereof. It will also be appreciated that it is immaterial whether the ECG electrodes are fixed to an interior or exterior surface of the wallet. It should further be noted that the electrode assembly may be a completely independent self-contained unit.

The invention claimed is:

1. An electrode assembly for a portable 12-lead ECG signaling device, said electrode assembly comprising a thin, flexible electrode support supporting a plurality of electrodes (V1, V2, V3, V4, V5 and V6, LA, RA, LL) at least some of which are constructed on the electrode support in proper spaced relationship for producing electrical contact with respective areas of a patient's chest for producing an electrocardiogram when the electrode assembly is placed directly against the patient's chest; wherein:

the flexible support comprises a plurality of foldable sections that fixedly support the electrodes thereon and open out to form a substantially flat base that is placeable against the patient's chest so that those of said electrodes that are in proper spaced relationship for producing electrical contact with respective areas of a patient's chest simultaneously contact the respective areas of the patient's chest without requiring adjustment or calibration, and whereby the electrode assembly can be folded into a compact unit prior to or after use, and one of the foldable sections is provided with a flap for tucking into a slot in another one of said sections, whereby the electrode assembly can be folded into a self-contained compact unit prior to use.

2. An electrode assembly for a portable 12-lead ECG signaling device, said electrode assembly comprising a thin, flexible electrode support supporting a plurality of electrodes (V1, V2, V3, V4, V5 and V6, LA, RA, LL) at least some of which are constructed on the electrode support in proper spaced relationship for producing electrical contact with respective areas of a patient's chest for producing an electrocardiogram when the electrode assembly is placed directly against the patient's chest; wherein:

the flexible support comprises a plurality of foldable sections that fixedly support the electrodes thereon and open out to form a substantially flat base that is placeable against the patient's chest so that those of said electrodes that are in proper spaced relationship for producing electrical contact with respective areas of a patient's chest simultaneously contact the respective areas of the patient's chest without requiring adjustment or calibration, and whereby the electrode assembly can be folded into a compact unit prior to or after use, and there is joined to at least one of the foldable sections a serpentine strip supporting thereon one of said electrodes (RA).

3. An electrode assembly for a portable 12-lead ECG signaling device, comprising:

a thin, flexible electrode support that is foldable into a compact unit prior to or after use, said electrode support supporting at least six electrodes (V1, V2, V3, V4, V5 and V6) wholly constructed on the electrode support in proper mutual spaced relationship for producing electrical contact each with a correct respective area of a patient's chest when two of said electrodes (V1, V2) are substantially symmetrically disposed about his or her vertebrae for producing a 12-lead electrocardiogram when the electrode assembly is placed flat against the patient's chest; and limb electrodes (LA, RA, LL) fixedly attached at one end thereof to the electrode support and having a second end displaceable from the electrode support for locating proximate a patient's limb;

wherein the electrode support has a plurality of foldable sections one of which is provided with a flap for tucking into a slot in another one of said sections, whereby the electrode assembly can be folded into a self-contained compact unit prior to use.

4. A wallet having the electrode assembly according to claim 3 integrally embedded therein.

5. The electrode assembly according to claim 3, wherein there is joined to the electrode support a serpentine strip supporting thereon one of said electrodes (RA).

6. The electrode assembly according to claim 3, wherein the electrodes are formed by a screen-printing technique.

7. The electrode assembly according to claim 3, further including a connector for removably connecting to the electrode assembly an electronic circuit.

8. The electrode assembly according to claim 7, being adapted for one time use.

9. The electrode assembly according to claim 3, wherein said electrode assembly comprises an ECG signaling device.

10. The electrode assembly according to claim 9, wherein said electrode assembly is integrally embedded in a wallet.

11. The device according to claim 9, including a vocalizing unit for producing an acoustic signal representative of the patient's ECG.

12. The device according to claim 11, including digital circuitry for producing a digital signal representative of the patient's ECG.

13. An electrode assembly for a portable 12-lead ECG signaling device, comprising:
- a thin, flexible electrode support that is foldable into a compact unit prior to or after use, said electrode support supporting at least six electrodes (V1, V2, V3, V4, V5 and V6) wholly constructed on the electrode support in proper mutual spaced relationship for producing electrical contact each with a correct respective area of a patient's chest when two of said electrodes (V1, V2) are substantially symmetrically disposed about his or her vertebrae for producing a 12-lead electrocardiogram when the electrode assembly is placed flat against the patient's chest; and
- limb electrodes (LA, RA, LL) fixedly attached at one end thereof to the electrode support and having a second end displaceable from the electrode support for locating proximate a patient's limb;
- wherein there is joined to the electrode support a serpentine strip supporting thereon one of said electrodes (RA).

14. The electrode assembly according to claim 13, wherein the electrodes are formed by a screen-printing technique.

15. The electrode assembly according to claim 13, wherein some of said electrodes are for male use exclusively and others are for female use exclusively.

16. The electrode assembly according to claim 13, further including a connector for removably connecting to the electrode assembly an electronic circuit.

17. The electrode assembly according to claim 13, being adapted for one time use.

18. A wallet having the electrode assembly according to claim 13 integrally embedded therein.

19. An ECG signaling device comprising an electrode assembly according to claim 13.

20. A wallet having the device according to claim 19 integrally embedded therein.

21. The device according to claim 19, including a vocalizing unit for producing an acoustic signal representative of the patient's ECG.

22. The device according to claim 21, including digital circuitry for producing a digital signal representative of the patient's ECG.

* * * * *